United States Patent [19]
Caruso

[11] Patent Number: 6,054,451
[45] Date of Patent: Apr. 25, 2000

[54] ANALGESIC COMPOSITION AND METHOD FOR ALLEVIATING PAIN

[75] Inventor: Frank S. Caruso, Colts Neck, N.J.

[73] Assignee: Algos Pharmaceutical Corporation, Neptune, N.J.

[21] Appl. No.: 09/063,754

[22] Filed: Apr. 21, 1998

[51] Int. Cl.[7] .......................... A01N 43/00; A61K 47/30; A61K 31/74; A61L 9/04; A61F 9/02
[52] U.S. Cl. .......................... 514/210; 424/45; 424/78.1; 424/464; 424/422; 424/436; 514/772.3
[58] Field of Search .............................. 424/400; 514/162, 514/289

[56] References Cited

U.S. PATENT DOCUMENTS

| | | | |
|---|---|---|---|
| 5,055,461 | 10/1991 | Kelleher et al. | 514/162 |
| 5,616,580 | 4/1997 | Olney | 514/266.2 |
| 5,834,479 | 11/1998 | Mayer et al. | 514/289 |

FOREIGN PATENT DOCUMENTS

| | | |
|---|---|---|
| WO9607412 | 3/1996 | WIPO . |
| 98/25920 | 6/1998 | WIPO . |

OTHER PUBLICATIONS

Decker et al. "Antionociceptive effects of the novel neuronal nicotinic acetlcholine receptor agonist, ABT–594, in mice", European, J. Pharmacology, vol. 346, No. 1, Apr. 3, 1998, pp. 23–33.

Weisenfeld–Hallin Z, "Combined Opioid–NMDA Antagonist Therapies", vol. 55, No. 1., Jan. 1998, pp. 1–4.

*Primary Examiner*—Thurman K. Page
*Assistant Examiner*—Todd D Ware
*Attorney, Agent, or Firm*—Dilworth & Barrese

[57] ABSTRACT

The analgesic effectiveness of an analgesic selected from the group consisting of (R)-5-(2-azetidinylmethoxy)-2-chloropyridine, (S)-5-(2-azetidinylmethoxy)-2-chloropyridine and pharmaceutically acceptable salts thereof is significantly potentiated by administering an analgesic-potentiating amount for said analgesic of at least one nontoxic NMDA receptor antagonist.

19 Claims, No Drawings

ANALGESIC COMPOSITION AND METHOD FOR ALLEVIATING PAIN

BACKGROUND OF THE INVENTION

This invention relates to an analgesic composition and method for alleviating pain. More particularly, this invention is concerned with alleviating pain by administering to a mammal exhibiting pain (a) an analgesia-effective amount of at least one analgesic selected from the group consisting of (R)-5-(2-azetidinylmethoxy)-2-chloropyridine, (S)-5-(2-azetidinylmethoxy)-2-chloropyridine and pharmaceutically acceptable salts thereof and (b) an analgesic-potentiating amount for said analgesic of at least one nontoxic antagonist, or blocker, for the N-methyl-D-aspartate (NMDA) receptor.

Administration of opioid analgesics such as morphine remains the most effective means of alleviating severe pain across a wide range of conditions that includes, for example, acute, persistent inflammatory and neuropathic pain. However, the use of opioid analgesics are limited due to side effects such as respiratory depression, constipation and physical dependence. Thus, efforts have been made to develop non-opioid analgesics for treatment of pain that are devoid of the problems associated with the opioid analgesics.

Recently, new members of the 3-pyridyl ether compounds, referred to as (R)-5-(2-azetidinylmethoxy)-2-chloropyridine (also referred to as ABT-594) and its S-enantiomer have been reported as being potent non-opioid analgesic agents. In general, these analgesics are believed to exert their analgesic action via the neuronal nicotinic acetylcholine receptors. The administration of the analgesics can result in pain management without the side effects associated with the administration of the opioid analgesics.

SUMMARY OF THE INVENTION

In accordance with the present invention, an analgesic composition for alleviating pain is provided which comprises (a) an analgesia-effective amount of at least one analgesic selected from the group consisting of (R)-5-(2-azetidinylmethoxy)-2-chloropyridine, (S)-5-(2-azetidinylmethoxy)-2-chloropyridine and pharmaceutically acceptable salts thereof; and, (b) an analgesic-potentiating amount for said analgesic of at least one nontoxic N-methyl-D-aspartate receptor antagonist.

Further in accordance with the present invention, a method of alleviating pain is provided which comprises administering to a mammal exhibiting pain (a) an analgesia-effective amount of at least one analgesic selected from the group consisting of (R)-5-(2-azetidinylmethoxy)-2-chloropyridine, (S)-5-(2-azetidinylmethoxy)-2-chloropyridine and pharmaceutically acceptable salts thereof; and, (b) an analgesic-potentiating amount for said analgesic of at least one nontoxic N-methyl-D-aspartate receptor antagonist.

The analgesic composition and method of alleviating pain of this invention are applicable to the treatment of all varieties of pain, e.g., arthritic pain, lumbosacral pain, musculo-skeletal pain, pain associated with a sore throat, etc. Thus, for a mammal in need of pain relief, an enhanced level of analgesia for an equivalent dosage of at least one analgesic, or an equivalent level of analgesia for a reduced dosage of at least one analgesic, can be achieved when at least one analgesic is administered prior to, with or following the administration of the nontoxic NMDA receptor antagonist.

The term "N-methyl-D-aspartate receptor" shall be understood to include all of the binding site subcategories associated with the NMDA receptor, e.g., the glycine-binding site, the phenylcyclidine (PCP)-binding site, etc., as well as the NMDA channel. Thus, the invention herein contemplates the use of nontoxic substances that block an NMDA receptor binding site, e.g., dextromethorphan, or block the NMDA channel, e.g., a source of magnesium such as magnesium sulfate.

The term "nontoxic" as used herein shall be understood in a relative sense and is intended to designate any substance that has been approved by the United States Food and Drug Administration ("FDA") for administration to humans or, in keeping with established regulatory criteria and practice, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 (the compound 5-methyl-10,11-dihydro-SH-dibenze[a,d] cyclohepten-5,10-imine), CPP (the compound 3-[2-carboxypiperazin-4-yl] propyl-1-phosphonic acid) and PCP (the compound 1-(1-phenylcyclohexyl)piperidine) whose toxicities effectively preclude their therapeutic use.

The terms "potentiate" and "potentiating" are used herein in their art-recognized sense, i.e., as referring to a significant increase in the level of pain-alleviating activity for the combination of the analgesic and nontoxic NMDA receptor antagonist of this invention compared with that which could have been expected based on the activities of the analgesic administered alone and nontoxic NMDA receptor antagonist administered alone.

The term "pain-alleviating" shall be understood herein to include the expressions "pain-suppressing" and "pain-inhibiting" as the invention is applicable to the alleviation of existing pain as well as the suppression or inhibition of pain which would otherwise ensue from an imminent pain-causing event.

The expression "analgesia-effective amount" as applied to the analgesic employed in the composition and method of this invention shall be understood to mean an amount of analgesic which when administered by itself or in combination with the nontoxic NMDA receptor antagonist provides significant analgesic activity.

DESCRIPTION OF THE PREFERRED EMBODIMENTS

The analgesic component of the analgesic composition of this invention is selected from the group consisting of (R)-5-(2-azetidinylmethoxy)-2-chloropyridine, (S)-5-(2-azetidinylmethoxy)-2-chloropyridine, pharmaceutically acceptable salts thereof and mixtures of any of the foregoing. These analgesics are known compounds and can be prepared by synthetic procedures as disclosed in U.S. Pat. No. 5,629,325, the contents of which are incorporated by reference herein.

Among the nontoxic substances that block the NMDA receptor and as such are useful for potentiating the analgesic activity of the foregoing analgesics in accordance with this invention are dextromethorphan ((+)-3-hydroxy-N-methylmorphinan), its metabolite dextrorphan ((+)-3-hydroxy-N-methylmorphinan), amantadine (1-amino adamantine), memantine (3,5 dimethylaminoadamantone), their mixtures and their pharmaceutically acceptable salts. Other useful nontoxic substances that block the NMDA receptor include pyrroloquinoline quinone, 4-hydroxy-2 (1H)-quinolone derivatives and cis-4-(phosphono-methyl)-2-piperidinecarboxylic acid. Of the foregoing nontoxic substances that block the NMDA receptor, dextromethorphan in the form of its hydrobromide salt is preferred for use herein due to its ready availablilty and its established use in over-the-counter medications where it functions as a cough suppressant.

With regard to dosage levels, the analgesic of this invention must be present in an analgesia-effective amount, e.g., at a level corresponding to the generally recommended adult human dosages for a particular analgesic, and the nontoxic NMDA receptor antagonist must be present at a level that potentiates the effectiveness of the analgesic. Given the wide variation in dosage level of the analgesic which depends to a large extent on the specific analgesic being administered, there can similarly be a wide variation in the dosage level of the nontoxic NMDA receptor antagonist. These amounts can be determined for a particular drug combination in accordance with this invention employing routine experimental testing.

While the analgesic and potentiating nontoxic NMDA receptor antagonist of this invention need not be administered together, they must both be present in the patient at effective levels at the same time. While it is within the scope of the invention to separately administer the analgesic and the nontoxic NMDA receptor antagonist, as a matter of convenience, it is preferred that these drugs be coadministered in a single dosage form. All modes of administrations are contemplated, e.g., orally, rectally, parenterally, topically, or by intravenous, intramuscular, intrastemal or subcutaneous injection or in a form suitable by inhalation. The formulations can, where appropriate, be conveniently presented in discrete dosage units and can be prepared by any of the methods well known in the art of pharmacy.

An analgesic composition containing the analgesic and nontoxic NMDA receptor antagonist will ordinarily be formulated with one or more pharmaceutically acceptable ingredients in accordance with known and established practice. Thus, the analgesic composition can be formulated as a liquid, powder, elixir, injectable solution, etc. Formulations for oral use can be provided as tablets or hard capsules wherein the pharmacologically active ingredients are mixed with an inert solid diluent such as calcium carbonate, calcium phosphate or kaolin, or as soft gelatin capsules wherein the active ingredients are mixed with water or miscible solvents such as propylene glycol; PEG's and ethanol, or an oleaginous medium, e.g., peanut oil, liquid paraffin or olive oil.

For topical administration in the mouth, the analgesic compositions can take the form of buccal or sublingual tablets, drops or lozenges formulated in conventional manner.

For topical administration to the epidermis the compounds of the invention can be formulated as creams, gels, ointments or lotions or as transdermal patches. Such compositions can, for example, be formulated with an aqueous or oily base with the addition of suitable thickening, gelling, emulsifying, stabilizing, dispersing, suspending, and/or coloring agents.

The compounds of the invention can also be formulated as depot preparations. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example as a sparingly soluble salt.

The compounds of the invention can be formulated for parenteral administration by injection, conveniently intravenous, intramuscular or subcutaneous injection, for example by bolus injection or continuous intravenous infusion. Formulations for injection can be presented in unit dosage from e.g. in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g. sterile pyrogen-free water, before use.

The compounds of the invention can also be formulated in rectal compositions such as suppositories or retention enemas. e.g. containing conventional suppository bases such as cocoa butter or other glyceride.

For intranasal administration, the compounds of the invention can be used, for example, as a liquid spray, as a powder or in the form of drops.

For administration by inhalation, the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit can be determined by providing a valve to deliver a metered amount. Capsules and cartridges of, for example, gelatin, for use in an inhaler or insulator can be formulated containing a powder mix of a compound of the invention and a suitable powder base such as lactose or starch.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

In addition to the analgesic and nontoxic NMDA receptor antagonist, the analgesic composition herein can contain at least one other pharmacologically active substance, e.g., a non-narcotic analgesic such as acetaminophen, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol, zomepirac, and the like or a narcotic analgesic such as codeine, dihydrocodeine, hydrocodone, levorphanol, morphine, oxycodone, and the like.

EXAMPLES 1–12

The following unit dosage forms are illustrative of the pain-alleviating drug combinations in accordance with the present invention:

| Example | Analgesic (mg) | Nontoxic NMDA Receptor Blocker (mg) | Additional Active Component (mg) |
|---|---|---|---|
| 1 | (R)-5-(2-azetidinylmethoxy)-2-chloropyridine (25) | dextromethorphan hydrobromide (30) | |
| 2 | (R)-5-(2-azetidinylmethoxy)-2-chloropyridine (25) | dextromethorphan hydrobromide (30) | acetaminophen (325) |
| 3 | (R)-5-(2-azetidinylmethoxy)-2-chloropyridine (25) | dextrorphan hydrobromide (30) | |
| 4 | (R)-5-(2-azetidinylmethoxy)-2-chloropyridine (25) | amantadine (30) | |
| 5 | (R)-5-(2-azetidinylmethoxy)-2-chloropyridine (25) | memantine (30) | |
| 6 | (R)-5-(2-azetidinylmethoxy)-2-chloropyridine (25) | memantine (30) | ibuprofen (325) |
| 7 | (S)-5-(2-azetidinylmethoxy)-2-chloropyridine (25) | dextromethorphan hydrobromide (30) | |
| 8 | (S)-5-(2-azetidinylmethoxy)-2-chloropyridine (25) | dextromethorphan hydrobromide (30) | acetaminophen (325) |
| 9 | (S)-5-(2-azetidinylmethoxy)-2-chloropyridine (25) | dextrorphan hydrobromide (30) | |
| 10 | (S)-5-(2-azetidinylmethoxy)-2-chloropyridine (25) | amantadine (30) | |
| 11 | (S)-5-(2-azetidinylmethoxy)-2-chloropyridine (25) | memantine (30) | |
| 12 | (S)-5-(2-azetidinylmethoxy)-2-chloropyridine (25) | memantine (30) | ibuprofen (325) |

In each of these dosage units, the nontoxic NMDA receptor antagonist dextromethorphan hydrobromide significantly potentiates the pain-alleviating activity of the analgesic.

What is claimed is:

1. An analgesic composition comprising (a) an analgesia-effective amount of at least one analgesic selected from the group consisting of (R)-5-(2-azetidinylmethoxy)-2-chloropyridine, (S)-5-(2-azetidinylmethoxy)-2-chloropyridine and pharmaceutically acceptable salts thereof; and, (b) an analgesic-potentiating amount for said analgesic of at least one nontoxic N-methyl-D-aspartate receptor antagonist.

2. The analgesic composition of claim 1 wherein the nontoxic NMDA receptor antagonist is at least one member selected from the group consisting of dextromethorphan, dextrorphan, amantadine, memantine and pharmaceutically acceptable salts thereof.

3. The analgesic composition of claim 1 wherein (a) and (b) each is present in the same or different sustained release carrier.

4. The analgesic composition of claim 1 containing a therapeutically effective amount of at least one other pharmaceutically active substance (c).

5. The analgesic composition of claim 4 wherein the pharmacologically active substance (c) is selected from the group consisting of non-narcotic analgesic and narcotic analgesic.

6. The analgesic composition of claim 5 wherein the non-narcotic analgesic is selected from the group consisting of acetaminophen, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol and zomepirac.

7. The analgesic composition of claim 5 wherein the narcotic analgesic is selected from the group consisting of codeine, dihydrocodeine, hydrocodone, levorphanol, morphine and oxycodone.

8. The analgesic composition of claim 5 wherein the nontoxic NMDA receptor antagonist is selected from the group consisting of dextromethorphan, dextrorphan, amantadine, memantine and pharmaceutically acceptable salts thereof.

9. The analgesic composition of claim 1 containing at least 15 mg (b).

10. The analgesic composition of claim 1 containing at least 20 mg (b).

11. A method of alleviating pain which comprises administering to a mammal exhibiting pain (a) an analgesia-effective amount of at least one analgesic selected from the group consisting of (R)-5-(2-azetidinylmethoxy)-2-chloropyridine, (S)-5-(2-azetidinylmethoxy)-2-chloropyridine and pharmaceutically acceptable salts thereof; and, (b) an analgesic-potentiating amount for said analgesic of at least one nontoxic N-methyl-D-aspartate receptor antagonist.

12. The method of claim 11 wherein the nontoxic NMDA receptor antagonist is at least one member selected from the group consisting of dextromethorphan, dextrorphan, amantadine, memantine and pharmaceutically acceptable salts thereof.

13. The method of claim 11 wherein (a) and (b) are coadministered.

14. The method of claim 11 wherein (a) and (b) are coadministered as a sustained release dosage form.

15. The method of claim 11 containing a therapeutically effective amount of at least one other pharmacologically active substance (c).

16. The method of claim 15 wherein the pharmacologically active substance (c) is selected from the group consisting of non-narcotic analgesic and narcotic analgesic.

17. The method of claim 15 wherein the non-narcotic analgesic is selected from the group consisting of acetaminophen, aspirin, diclofenac, diflusinal, etodolac, fenbufen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol and zomepirac.

18. The method of claim 15 wherein the narcotic analgesic is selected from the group consisting of codeine, dihydrocodeine, hydrocodone, levorphanol, morphine and oxycodone.

19. The method of claim 15 wherein the nontoxic NMDA receptor antagonist is selected from the group consisting of dextromethorphan, dextrorphan, amantadine, memantine and pharmaceutically acceptable salts thereof.

* * * * *

UNITED STATES PATENT AND TRADEMARK OFFICE
CERTIFICATE OF CORRECTION

PATENT NO.: 6,054,451

DATED: April 25, 2000

INVENTOR(S): Frank S. Caruso

It is certified that error appears in the above-identified patent and that said Letters Patent is hereby corrected as shown below:

Page 1, Other Publications, line 1, change "Antionociceptive" to -- Antinociceptive --

Page 1, Other Publications, line 2, change "acetlcholine" to -- acetylcholine --

Page 1, Other Publications, line 6, after "Therapies"," insert -- DRUGS --

Column 4, line 40, change "e.g," to -- e.g., --

Column 4, line 54, change "diflusinal" to -- diflunisal --

Column 6, line 65, change "diflusinal to -- diflunisal --

Signed and Sealed this

First Day of May, 2001

*Attest:*

NICHOLAS P. GODICI

*Attesting Officer*   *Acting Director of the United States Patent and Trademark Office*